(12) United States Patent
Belliard et al.

(10) Patent No.: US 8,163,025 B2
(45) Date of Patent: Apr. 24, 2012

(54) DISC PROSTHESIS FOR CERVICAL VERTEBRAE

(75) Inventors: Karl Belliard, La Membrolle sur Longuenee (FR); Régis Le Couëdic, Andresy (FR); Paolo Mangione, Pessac (FR); Jacques Senegas, Merignac (FR)

(73) Assignee: Zimmer Spine, Inc., Minneapolis, MN (US)

( * ) Notice: Subject to any disclaimer, the term of this patent is extended or adjusted under 35 U.S.C. 154(b) by 849 days.

(21) Appl. No.: 12/096,312

(22) PCT Filed: Dec. 13, 2006

(86) PCT No.: PCT/FR2006/051343
§ 371 (c)(1),
(2), (4) Date: Oct. 27, 2008

(87) PCT Pub. No.: WO2007/074265
PCT Pub. Date: Jul. 5, 2007

(65) Prior Publication Data
US 2009/0222094 A1 Sep. 3, 2009

(30) Foreign Application Priority Data

Dec. 26, 2005 (FR) ..................................... 05 54091

(51) Int. Cl.
*A61F 2/44* (2006.01)

(52) U.S. Cl. .................................................. 623/17.15
(58) Field of Classification Search ..... 623/17.11–17.16
See application file for complete search history.

(56) References Cited

U.S. PATENT DOCUMENTS

| 6,517,580 | B1 | 2/2003 | Ramadan et al. | |
|---|---|---|---|---|
| 7,563,286 | B2 * | 7/2009 | Gerber et al. | ............... 623/17.14 |
| 2004/0133278 | A1 | 7/2004 | Marino et al. | |
| 2005/0033438 | A1 | 2/2005 | Schultz et al. | |
| 2005/0080488 | A1 | 4/2005 | Schultz | |

FOREIGN PATENT DOCUMENTS

FR 2 730 159 A1 8/1996

* cited by examiner

*Primary Examiner* — Anu Ramana
(74) *Attorney, Agent, or Firm* — Seager Tufte & Wickhem LLC

(57) ABSTRACT

A disc prosthesis for vertebrae is provided. The disc prosthesis comprises a first plate, a first insert, a second plate, and a second insert. The first plate comprises a first active face and a first anchor face. The second plate comprises a second active face and a second anchor face. The first anchor face is configured to anchor the first plate to a first vertebra. The second anchor face is configured to anchor the second plate to a second vertebra. The first plate comprises a cavity for receiving the first insert. The cavity comprises a concave spherical cap. The second plate comprises an opening that connects the second active face to the second anchor face. The second insert comprises a fastener portion, said fastener portion is friction fit in the opening.

10 Claims, 2 Drawing Sheets

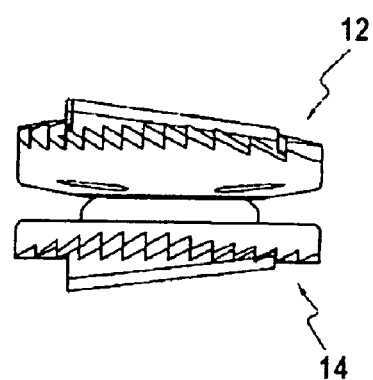
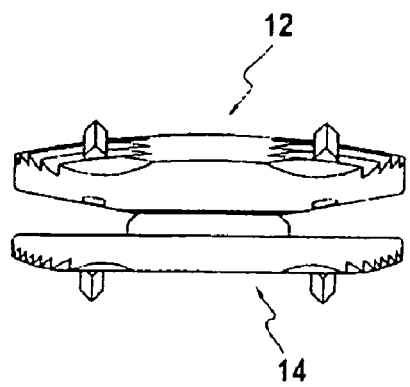
FIG.1  FIG.2
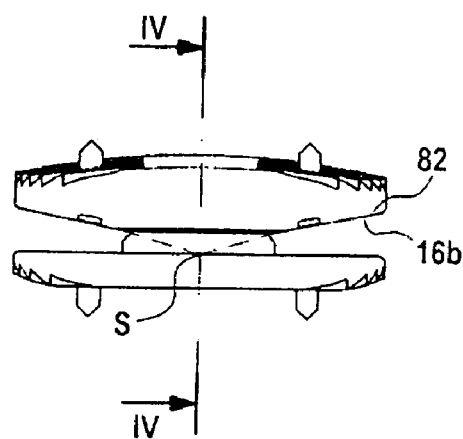
FIG.3
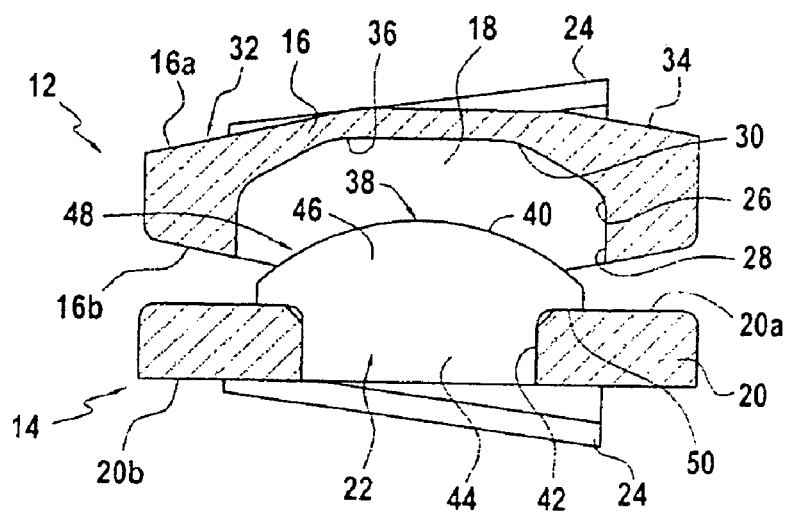
FIG.4

DISC PROSTHESIS FOR CERVICAL VERTEBRAE

CROSS REFERENCE TO RELATED APPLICATIONS

This application is the National Stage of International Application No. PCT/FR2006/051343, filed on Dec. 13, 2006, which claims priority to French Patent Application Number 0554091, filed on Dec. 26, 2005, the contents of both of which are hereby are incorporated by reference as if fully set forth herein.

BACKGROUND OF THE INVENTION

1. Field of the Invention

The present invention relates to a cervical disk prosthesis.

2. Description of Related Art

Cervical disk prostheses are implants for taking the place of the natural intervertebral disk that lies between cervical vertebrae.

In known manner, these prostheses comprise a top assembly and a bottom assembly, together defining a ball-joint system constituted by at least two plates designed to be anchored in the vertebral plates of two adjacent vertebrae. These plates themselves, or by means of inserts, define a dome, i.e. a convex spherical cap, and a cup, i.e. a concave spherical cap. Co-operation between these two spherical caps constitutes a ball-joint system that conserves relative mobility between the vertebrae that is substantially equal to that provided by the natural intervertebral disk.

Usually, these prostheses are made of chromium-cobalt alloy. That material is entirely biocompatible.

Nevertheless, that material presents the drawback of not being transparent to medical imaging, e.g. by means of magnetic resonance imaging (MRI) or by means of a scanner. The presence in the body of a patient of a chromium-cobalt prosthesis disturbs the image that can be obtained using those techniques.

To remedy that drawback, it is known to use another material, polyetheretherketone (PEEK) that presents very good biocompatibility properties, and that is transparent to medical imaging. Nevertheless, that material presents mechanical properties and suitability for machining that are very different from those of chromium-cobalt.

SUMMARY OF THE INVENTION

An object of the present invention is to provide a cervical disk prosthesis that is made essentially out of a material that is entirely transparent to medical imaging, while nevertheless presenting mechanical characteristics that are compatible with the type of prosthesis in question.

To achieve this object, the invention provides a disk prosthesis for cervical vertebrae that comprises first and second assemblies, each constituted by a prosthetic plate and by and insert, the plate having an active face and an anchor face for anchoring in a vertebra. It is characterized in that:

said prosthetic plates and said inserts are made respectively of first and second materials that are biocompatible and substantially transparent to medical imaging;

the plate of the first assembly includes a non-through cavity in its anchor face for receiving said first insert that defines a concave spherical cap;

the plate of the second assembly includes an orifice that opens out into both of its faces; and said second insert comprises a fastener portion engaged by force in the orifice of the second prosthetic plate and a portion forming a convex spherical cap of outside dimensions that are greater than the dimensions of the orifice so as to constitute a shoulder bearing on the active face of the second prosthetic plate;

and in that it further comprises anchor fins, said anchor fins being made of a material that is biocompatible and not transparent to medical imaging, each fin having fastener extensions suitable for penetrating by force into fastener holes formed in the plates, the fastener holes of the first plate lying, in projection onto a plane perpendicular to the axis of the first insert, outside the outline of the cavity formed in the first plate, and the fastener holes of the second plate lying, in projection onto a plane perpendicular to the axis of the second insert, outside the projection of the periphery of the portion of the second insert that forms a convex spherical cap.

It will be understood firstly that because the two prosthetic plates and the two inserts are made using materials that are transparent to medical imaging, while the small-sized anchor fins are made of a material that is not transparent to medical imaging, a prosthesis is obtained that is compatible overall with medical imaging, while still making it possible to detect the exact position on the prosthesis because of the material from which the anchor fins are made.

It will also be understood that the connection between the second plate and the second insert ensures maximum force take-up and that the particular position of the anchor fin fastener holes make it possible to avoid weakening the prosthetic plate.

Another advantage of the invention is that since each assembly is made up of two parts, it is possible to adopt different machining techniques for those two parts, matching them to the functions performed.

Preferably, the prosthetic plates are made of PEEK.

Also preferably, the inserts are made of ceramic.

Also preferably, the anchor fins are made of titanium.

In a preferred embodiment, each prosthetic plate presents a plane of symmetry containing the axis of the insert that corresponds thereto, and the anchor face of each prosthetic plate includes anchoring portions in relief, said portions in relief being disposed on either side of the plane of symmetry, leaving a central zone on the anchor face that does not have portions in relief.

This provision serves to ensure that making the portions in relief does not reduce the thickness of the central portions of the prosthetic plates that include the cavity or the orifice used for mounting the inserts.

In a likewise preferred embodiment, the face of the first insert opposite from the face forming the concave spherical cap is generally dome-shaped so that the thickness of the first insert in the direction of its axis is substantially constant.

It will be understood that because of the domed shape of the first insert, it is likewise ensured that the prosthetic plate itself is of substantially constant thickness in the direction of the axis of the insert, and thus of the corresponding prosthetic plate.

BRIEF DESCRIPTION OF THE DRAWINGS

Other characteristics and advantages of the invention appear better on reading the following description of an embodiment of the invention given by way of non-limiting examples. The description refers to the accompanying figures, in which:

FIG. 1 is a side view of the disk prosthesis;

FIG. 2 is a posterior view of the prosthesis as a whole;

FIG. 3 is an anterior view of the prosthesis as a whole;

FIG. 4 is a vertical section view on line IV-IV of FIG. 3;

DETAILED DESCRIPTION

Figure 5A:
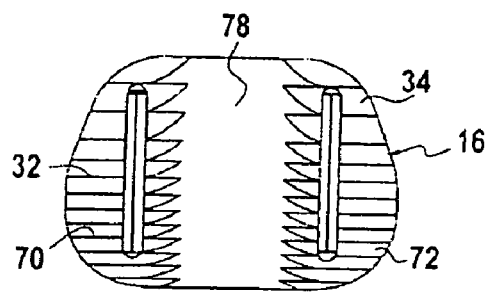
FIGS. 5A, 5B, and 5C are respectively a plan view, a posterior view, and an underside view of the first prosthetic plate.

The main component elements of the cervical disk prosthesis are described initially with reference to FIG. 4. This prosthesis comprises a top assembly 12 and a bottom assembly 14. The top assembly 12 is itself made up of a top prosthetic plate 16 and a top insert 18, while the bottom assembly 14 is constituted by a prosthetic plate 20 and by an insert 22. The prosthesis also comprises anchor fins 24 for each of the top and bottom assemblies 12 and 14 respectively.

The top plate 16 of the top assembly 12 presents an anchor top face 16a and an active bottom face 16b. The bottom face 16b of the face 16b of the plate 16 has a cavity 26 formed therein that comprises a substantially cylindrical portion 28 and a dome-shaped top. The dome-shaped top 30 of the cavity corresponds to sloping lateral portions 32 and 34 of the anchor face 16a such that the remaining thickness of the prosthetic plate in this zone is substantially constant.

The top insert 18 presents an embedding face 36 of shape that exactly matches the inside face of the cavity 26. The insert 18 has an active face 38 with a central portion that defines a concave spherical cap 40. The top prosthetic plate 16 and the insert 18 share a common plane of symmetry.

The bottom prosthetic plate 20 presents a substantially cylindrical orifice 42 in its central portion that opens out into its active top face 20a and into its anchor bottom face 20b. The bottom insert 22 has an engagement first portion 44 that is substantially cylindrical, being of a shape that corresponds exactly to the shape of the orifice 42 formed in the bottom prosthetic plate 20. It also has an active portion 46 that defines a convex spherical cap 48 suitable for co-operating with the concave spherical cap 40 of the insert 18. As shown in FIG. 4, the top portion of the insert 22 has an outside diameter greater than that of the engagement portion 44 so as to define a shoulder 50 that rests on the top face 20a of the prosthetic plate 20.

In the preferred embodiment, the inserts 18 and 22 are made of ceramic, while the prosthetic plates 16 and 20 are made of PEEK.

Figure 7:
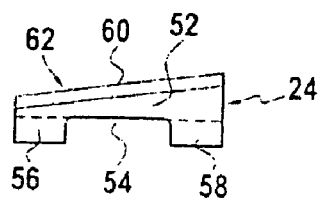
FIG. 7 is a side view of an anchor fin.

In FIG. 7, there can be seen a side view of a preferred embodiment of an anchor fin 44. It is generally in the form of a right angled triangle 52 with the long side 54 of the right angle being provided at its ends with two fastening projections 56 and 58. The hypotenuse 60 of the triangle constitutes the anchor portion proper of the fin and preferably presents a sharp edge 62. Naturally, the fin could have a different active portion 52.

To fasten the anchor fins 24 respectively in the top prosthetic plate 16 and in the bottom prosthetic plate 20, pairs of holes 64 and 66 are made passing right through the top prosthetic plate. For the bottom prosthetic plate 20, there are pairs of fastener holes 68 and 70. As can be seen clearly in FIG. 5C, the fastener holes 64 and 66 of the top prosthetic plate are located outside the periphery of the top insert 18. In the same manner, the fastener holes of the bottom prosthetic plate 20 are disposed outside the periphery of the portion 48 of the insert 22 that constitutes the convex spherical cap.

The fastener projections 56 and 58 of the anchor fins 24 are engaged by force in the pairs of fastener holes 64, 66, 68, and 70.

Given the positions of the fastener holes 64, 66, 68, and 70, it will be understood that the prosthetic plate is not weakened in the zone where it presents reduced thickness, at least so far as the top prosthetic plate 16 is concerned.

Figure 6A:
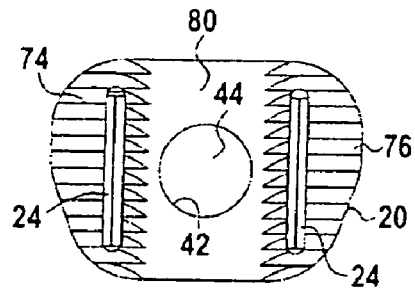
FIGS. 6A, 6B and 6C are respectively a plan view, an anterior view, and a view from below of the second assembly forming the prosthesis.
Figure 5B:
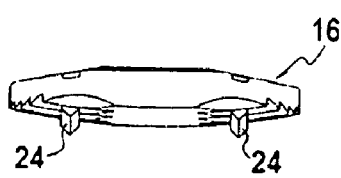
Figure 6B:
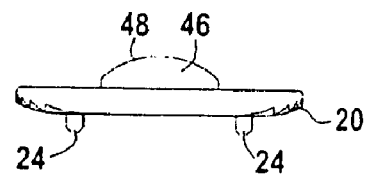
Figure 5C:
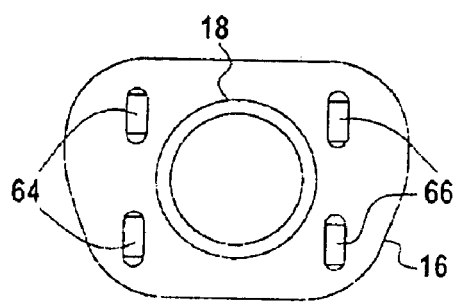
Figure 6C:
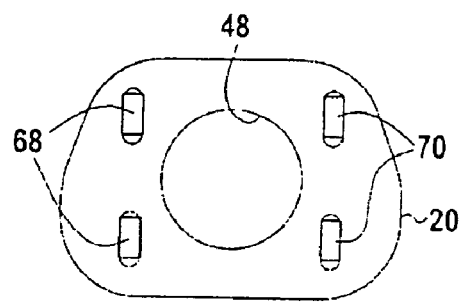

As shown in FIGS. 5A and 6A, the anchor faces of the prosthetic plates are also provided with two zones of portions in relief constituted in this particular example by serrations of direction parallel to the width of the plate. For the top prosthetic plate 15, there are serrations zones 71 and 72, and for the bottom prosthetic plate 20, there are serration zones 74 and 76. The serration zones 71 and 72 of the top prosthetic plate 16 are disposed on either side of the control zone occupied by the cavity 26. In the particular embodiment described, the serration zones are disposed in the inclined portions 32 and 34 of the anchor face, leaving a central zone 78 that does not have any portions in relief so as to avoid reducing the remaining thickness of the prosthetic plate in the zone of the cavity 26. Similarly, the zones 74 and 76 of portions in relief of the bottom prosthetic plate are disposed on either side of the orifice 44 formed in the prosthetic plate for fastening the insert 22, thus leaving free a central zone 80 that does not have any serrations. The reason for positioning the serration zones 74 and 76 of the bottom prosthetic plate 20 are the same as those for positioning the serration zones 71 and 72 of the top prosthetic plate 16.

In FIGS. 2 and 3, it can also be seen that the portion of the active face 16b extending around the cavity 26 that contains the insert 18 is itself in the form of a truncated cone 82, with the vertex S of the truncated cone 82 being located outside the top assembly 12. By means of this disposition, the amplitude of the ball-joint movement between the top assembly 12 and the bottom assembly 14 is thus increased.

It should also be specified that the assembly fins 24 serve to enable the prosthetic plate to be pre-anchored in the vertebral plate. The serration zones 71, 72, 74, and 76 subsequently enhance this anchoring by virtue of bony tissue growing within the serrations.

The invention claimed is:

1. A disc prosthesis for vertebrae, said disc prosthesis comprising:
    a first assembly; and
    a second assembly,
    wherein the first assembly comprises a first plate;
    wherein the second assembly comprises a second plate,
    wherein the first plate comprises a first active face and a first anchor face;
    wherein the second plate comprises a second active face and a second anchor face,
    wherein the first anchor face is configured to anchor the first assembly to a first vertebra, wherein the second anchor face is configured to anchor the second assembly to a second vertebra,
    wherein the first assembly comprises a first insert;
    wherein the second assembly comprises a second insert;
    wherein the first and second plates are made of a first material, said first material being biocompatible and substantially transparent to medical imaging;
    wherein the first and second inserts are made of a second material, said second material being biocompatible and substantially transparent to medical imaging;
    wherein the first plate comprises a cavity for receiving the first insert,
    wherein the first insert comprises a concave spherical cap, wherein the second plate comprises an opening that connects the second active face to the second anchor face, wherein the second insert comprises a fastener portion, said fastener portion is configured to friction fit in the opening, wherein the second insert comprises a convex spherical cap, wherein the outside diameter of the convex spherical cap is greater than the diameter of the opening so as to form a shoulder configured to bear on the second active face;

wherein the first assembly and the second assembly each comprise anchor fins, wherein said anchor fins comprise a material that is biocompatible and not transparent to medical imaging, wherein said anchor fins each comprises a fastener extension configured to engage by force into a fastener hole formed in the first plate or the second plate, wherein a first fastener hole and a second fastener hole of the first plate lie in a plane perpendicular to an axis of the first insert, the first fastener hole and the second fastener hole lying in a region of the first plate outside the periphery of the cavity formed in the first plate, and wherein a third fastener hole and a fourth fastener hole of the second plate lie in a plane perpendicular to the axis of the second insert, the third fastener hole and the fourth fastener hole lying in a region of the second plate outside the periphery of the convex spherical cap of the second plate.

2. A prosthesis according to claim 1, wherein the first and second plates are made of PEEK.

3. A prosthesis according to claim 1, wherein the first and second inserts are made of ceramic.

4. A prosthesis according to claim 1, wherein the anchor fins are made of titanium.

5. A prosthesis according to claim 1, wherein the first and second anchor faces each comprise anchoring portions.

6. The prosthesis according to claim 5,
wherein the first and second plates have a plane of symmetry, and
wherein the anchoring portions are disposed on either side of the plane of symmetry, leaving a central zone on the anchor faces that does not have anchoring portions.

7. A prosthesis according to claim 1, wherein the first active face surrounds the first insert to form a frustoconical shape.

8. A prosthesis according to claim 1, wherein the first insert is engaged in the cavity of the first plate.

9. A prosthesis according to claim 1, wherein each anchor fin is generally triangular in shape and comprises two extensions, each extension extending from an end of the base of the triangle.

10. A prosthesis according to claim 1, wherein when the prosthesis is in placed between two adjacent vertebral bodies, the first assembly forms a top assembly and the second assembly forms a bottom assembly.

* * * * *